United States Patent
Govari et al.

(10) Patent No.: US 10,441,354 B2
(45) Date of Patent: Oct. 15, 2019

(54) TEMPERATURE CONTROLLED SHORT DURATION ABLATION

(71) Applicant: BIOSENSE WEBSTER (ISRAEL) LTD., Yokneam (IL)

(72) Inventors: Assaf Govari, Haifa (IL); Yaron Ephrath, Karkur (IL); Andres Claudio Altmann, Haifa (IL); Israel Zilberman, Yokneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 388 days.

(21) Appl. No.: 15/179,167

(22) Filed: Jun. 10, 2016

(65) Prior Publication Data
US 2017/0209210 A1  Jul. 27, 2017

Related U.S. Application Data

(60) Provisional application No. 62/286,534, filed on Jan. 25, 2016.

(51) Int. Cl.
*A61B 18/14* (2006.01)
*A61B 18/00* (2006.01)
*A61B 90/00* (2016.01)

(52) U.S. Cl.
CPC ............ *A61B 18/1492* (2013.01); *A61B 2018/00029* (2013.01); *A61B 2018/00351* (2013.01);
(Continued)

(58) Field of Classification Search
CPC ...... A61B 18/1492; A61B 2018/00029; A61B 2018/00666; A61B 2018/00678; A61B 2018/00702; A61B 2018/00875
See application file for complete search history.

(56) References Cited

U.S. PATENT DOCUMENTS

| | | | |
|---|---|---|---|
| 5,540,681 A | 7/1996 | Strul et al. | |
| 5,573,533 A | 11/1996 | Strul | |

(Continued)

FOREIGN PATENT DOCUMENTS

| | | |
|---|---|---|
| EP | 2662116 A1 | 11/2013 |
| EP | 2942023 A2 | 11/2015 |
| EP | 2954865 A1 | 12/2015 |

OTHER PUBLICATIONS

European Search Report dated Jul. 11, 2017 in corresponding European Patent Application No. 17152784.9.

(Continued)

*Primary Examiner* — Lee S Cohen
*Assistant Examiner* — Tigist S Demie
(74) *Attorney, Agent, or Firm* — Lewis Roca Rothgerber Christie LLP

(57) ABSTRACT

A method, including selecting a first maximum radiofrequency (RF) power to be delivered by an electrode within a range of 70 W-100 W, and selecting a second maximum RF power to be delivered by the electrode within a range of 20 W-60 W. The method also includes selecting an allowable force on the electrode within a range of 5 g-50 g, selecting a maximum allowable temperature, of tissue to be ablated, within a range of 55° C.-65° C., and selecting an irrigation rate for providing irrigation fluid to the electrode within a range of 8-45 ml/min. The method further includes performing an ablation of tissue using the selected values by initially using the first power, switching to the second power after a predefined time between 3 s and 6 s, and terminating the ablation after a total time for the ablation between 10 s and 20 s.

16 Claims, 4 Drawing Sheets

(52) U.S. Cl.
CPC ............... *A61B 2018/00577* (2013.01); *A61B 2018/00666* (2013.01); *A61B 2018/00678* (2013.01); *A61B 2018/00702* (2013.01); *A61B 2018/00791* (2013.01); *A61B 2018/00875* (2013.01); *A61B 2090/065* (2016.02)

(56) References Cited

U.S. PATENT DOCUMENTS

| | | | |
|---|---|---|---|
| 5,971,980 | A | 10/1999 | Sherman |
| 6,106,524 | A | 8/2000 | Eggers et al. |
| 7,207,989 | B2 | 4/2007 | Pike, Jr. et al. |
| 8,641,705 | B2 | 2/2014 | Leo et al. |
| 8,882,761 | B2 | 11/2014 | Desai |
| 2002/0077627 | A1 | 6/2002 | Johnson et al. |
| 2002/0123749 | A1 | 9/2002 | Jain |
| 2002/0151884 | A1 | 10/2002 | Hoey et al. |
| 2003/0069573 | A1 | 4/2003 | Kadhiresan et al. |
| 2003/0158551 | A1* | 8/2003 | Paton ............... A61B 18/1206 606/51 |
| 2004/0193148 | A1 | 9/2004 | Wham et al. |
| 2006/0287649 | A1 | 12/2006 | Ormsby et al. |
| 2008/0114351 | A1* | 5/2008 | Irisawa ............ A61B 18/1206 606/41 |
| 2009/0187183 | A1 | 7/2009 | Epstein |
| 2009/0234351 | A1* | 9/2009 | Desinger ........... A61B 18/1206 606/35 |
| 2010/0057072 | A1 | 3/2010 | Roman et al. |
| 2010/0168736 | A1 | 7/2010 | Wang |
| 2010/0298826 | A1 | 11/2010 | Leo et al. |
| 2011/0009857 | A1 | 1/2011 | Subramaniam et al. |
| 2011/0130648 | A1 | 6/2011 | Beeckler et al. |
| 2011/0224573 | A1 | 9/2011 | Bar-Tal et al. |
| 2012/0123400 | A1 | 5/2012 | Francischelli et al. |
| 2013/0282084 | A1 | 10/2013 | Mathur et al. |
| 2014/0171821 | A1 | 6/2014 | Govari et al. |
| 2014/0275993 | A1 | 9/2014 | Ballakur |
| 2015/0088119 | A1 | 3/2015 | Moss |
| 2015/0272655 | A1 | 10/2015 | Condie et al. |

OTHER PUBLICATIONS

European Search Report dated Jul. 11, 2017 in corresponding European Patent Application No. 17152848.2.
European Search Report dated Jul. 11, 2017 in corresponding European Patent Application No. 17152826.8.
European Search Report dated Aug. 17, 2017 in corresponding European Patent Application No. 17152786.4.
Topp, Stefan A., M.D. et al., "Saline-Linked Surface Radiofrequency Ablation Factors Affecting Steam Popping and Depth of Injury in the Pig Liver", Annals of Surgery, Apr. 2004, pp. 518-527, vol. 239, No. 4.

* cited by examiner

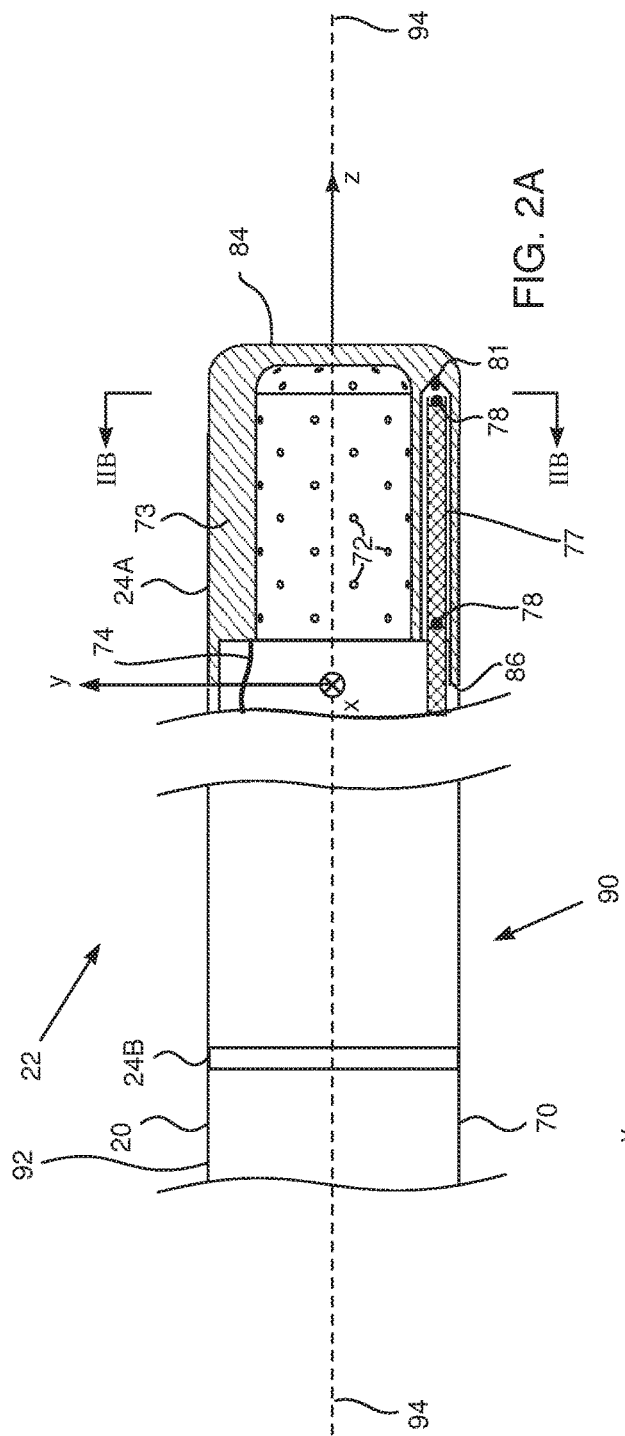
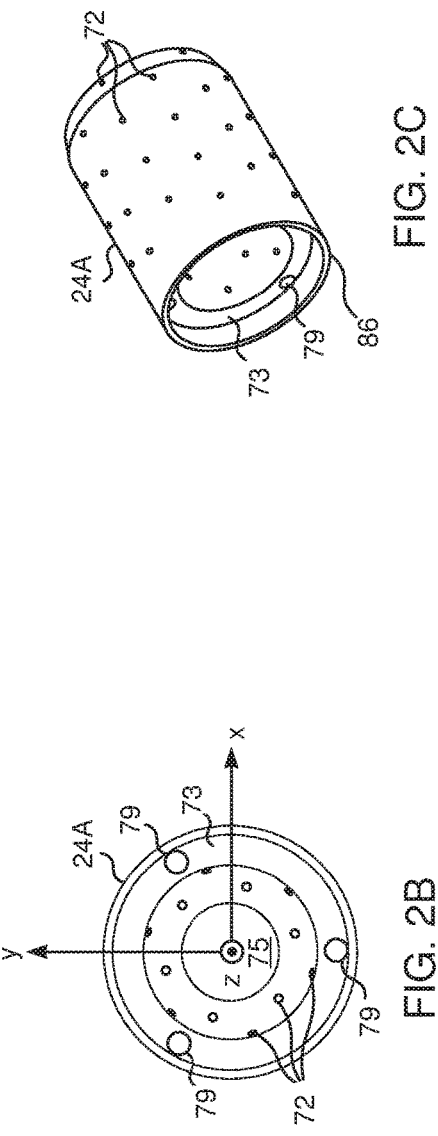

TEMPERATURE CONTROLLED SHORT DURATION ABLATION

CROSS-REFERENCE TO RELATED APPLICATION

This application claims the benefit of U.S. Provisional Patent Application 62/286,534, filed Jan. 25, 2016, which is incorporated herein by reference.

FIELD OF THE INVENTION

The present invention relates generally to surgery, and specifically to surgery using radiofrequency ablation.

BACKGROUND OF THE INVENTION

Radiofrequency (RF) ablation is a treatment modality that kills unwanted tissue by heat. Starting with cardiac arrhythmia treatment in the 1980s, RF ablation has found clinical application in a number of diseases, and is now the treatment of choice for certain types of cardiac arrhythmia, and certain cancers. During RF ablation, an electrode is inserted into proximity with the target region under medical imaging guidance. Tissue surrounding the electrode in the target region is destroyed by heating via RF electric current.

RF ablation is typically performed at continuous power levels of the order of 20-50 watts, with a contact force of approximately 10 g, and under irrigation. The time of ablation, depending on the size of the lesion to be achieved, is typically approximately 1 minute. In general, higher power levels reduce the time needed for forming a specific lesion. However, in prior art systems large values of continuous power cannot be used because of the danger of steam pops being formed.

US Patent Application 2010/0057072, to Roman et al., whose disclosure is incorporated herein by reference, describes an ablation catheter for performing tissue ablation. The disclosure states that RF energy may be safely delivered potentially at wattages up to 100 W.

U.S. Pat. No. 7,207,989, to Pike Jr. et al., whose disclosure is incorporated herein by reference, describes a method for ablating tissue in or around the heart to create an enhanced lesion. The distal end of a needle electrode is introduced into the tissue. An electrically-conductive fluid is infused through the needle electrode and into the tissue. The tissue is ablated after and/or during introduction of the fluid into the tissue.

US Patent Application 2015/0272655, to Condie et al., whose disclosure is incorporated herein by reference, describes a system for preventing unintended tissue damage from the delivery of unintended bipolar radiofrequency energy. The disclosure states that if 100 watts of RF energy is being delivered but only 10 watts is required to produce a desired electrode temperature, an electrode may be activated for 10% of a given period of time and deactivated for 90% of that duration of time.

U.S. Pat. No. 8,641,705, to Leo et al., whose disclosure is incorporated herein by reference, describes an apparatus for controlling lesion size in catheter-based ablation treatment. The apparatus measures the force exerted by a contact ablation probe on a target tissue and integrates the force over an energization time of the ablation probe. The force-time integral can be calculated and utilized to provide an estimated lesion size (depth, volume and/or area) in real time.

U.S. Pat. No. 8,882,761, to Desai, whose disclosure is incorporated herein by reference, describes a catheter for ablation. The disclosure refers to commonly practiced ablation procedure, and states that in such a procedure 35 to 50 watts of power is delivered at 40 to 50 degree Celsius through a temperature controlled Radiofrequency Generator, and that the saline irrigation fluid rate during the ablation is 30 ml/min.

US Patent Application 2011/0009857, to Subramaniam et al., whose disclosure is incorporated herein by reference, describes an open-irrigated catheter with turbulent flow. Pressurized fluid is delivered from a fluid lumen of a catheter body into an ablation electrode. Fluid flow in the fluid lumen is generally laminar. The generally laminar fluid flow is transformed from the fluid lumen into a turbulent fluid flow within the ablation electrode.

In an article by Topp et al., entitled "Saline-linked surface radiofrequency ablation: Factors affecting steam popping and depth of injury in the pig liver," Ann. Surg., vol. 239, no. 4, pp. 518-27 (2004), the authors claim to have determined parameters that predict steam popping, and depth of tissue destruction under nonpopping conditions. The article is incorporated herein by reference.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

selecting a maximum radiofrequency (RF) power to be delivered by an electrode within a range of 70 W-100 W;

selecting an allowable force on the electrode within a range of 5 g-50 g;

selecting a maximum allowable temperature, of tissue to be ablated, within a range of 55° C.-65° C.;

selecting an irrigation rate for providing irrigation fluid to the electrode within a range of 8-45 ml/min; and performing an ablation of the tissue using the selected values.

In a disclosed embodiment the selected values are: maximum RF power 90 W, allowable force between 10 g and 20 g, maximum allowable temperature 60° C., and irrigation rate 15 ml/min, and the power is delivered for 3 s so as to provide a lesion having a depth between 1 mm and 3 mm.

In a further disclosed embodiment the selected values are: maximum RF power 90 W, allowable force between 10 g and 20 g, maximum allowable temperature 60° C., and irrigation rate 15 ml/min, and the power is delivered for 3 s, and is then reduced to 50 W so as to provide a lesion having a depth between 4 mm and 5 mm.

In a yet further disclosed embodiment the method includes measuring an impedance to an RF power delivered by the electrode during the ablation, and, when a change in the impedance exceeds a preset value, halting the ablation of the tissue. Typically, the change is at least 7Ω.

In an alternative embodiment the method includes measuring at respective times a temperature of the tissue, and, when the temperature exceeds the selected maximum allowable temperature, reducing a level of an RF power delivered by the electrode. Typically, the temperature is measured at a frequency of at least 30 Hz.

There is further provided, according to an embodiment of the present invention, a method, including:

selecting a first maximum radiofrequency (RF) power to be delivered by an electrode within a range of 70 W-100 W;

selecting a second maximum RF power to be delivered by the electrode within a range of 20 W-60 W;

selecting an allowable force on the electrode within a range of 5 g-50 g;

selecting a maximum allowable temperature, of tissue to be ablated, within a range of 55° C.-65° C.;

selecting an irrigation rate for providing irrigation fluid to the electrode within a range of 8-45 ml/min; and performing an ablation of tissue using the selected values by initially using the first power, switching to the second power after a predefined time between 3 s and 6 s, and terminating the ablation after a total time for the ablation between 10 s and 20 s.

In a disclosed embodiment the method includes measuring an impedance to an RF power delivered by the electrode during the ablation, and, when a change in the impedance exceeds a preset value, halting the ablation of the tissue. Typically, the change is at least 7Ω.

In a further disclosed embodiment the method includes measuring at respective times a temperature of the tissue, and, when the temperature exceeds the selected maximum allowable temperature, reducing a level of an RF power delivered by the electrode. Typically the temperature is measured at a frequency of at least 30 Hz.

There is further provided, according to an embodiment of the present invention, a method, including:

performing an ablation procedure on biological tissue using radiofrequency (RF) power;

measuring an impedance to the RF power during the procedure; and when a change in the impedance exceeds a preset value, halting supply of the RF power to the tissue. Typically, the change is at least 7Ω.

There is further provided, according to an embodiment of the present invention, a method, including:

performing an ablation procedure on biological tissue using radiofrequency (RF) power;

measuring at respective times a temperature of the tissue; and when the temperature exceeds a preset maximum allowable temperature, reducing a level of the RF power supplied to the tissue. Typically, the temperature of the tissue is measured at a frequency of at least 30 Hz.

There is further provided, according to an embodiment of the present invention, apparatus, including:

an electrode;

a power control module configured to select a maximum radiofrequency (RF) power to be delivered by the electrode within a range of 70 W-100 W; and a processor coupled to the power control module and configured to:

select an allowable force on the electrode within a range of 5 g-50 g;

select a maximum allowable temperature, of tissue to be ablated, within a range of 55° C.-65° C.;

select an irrigation rate for providing irrigation fluid to the electrode within a range of 8-45 ml/min; and perform an ablation of the tissue using the selected values.

There is further provided, according to an embodiment of the present invention, apparatus, including:

an electrode;

a power control module configured to select a first maximum radiofrequency (RF) power to be delivered by the electrode within a range of 70 W-100 W and to select a second maximum RF power to be delivered by the electrode within a range of 20 W-60 W; and a processor coupled to the power control module and configured to:

select an allowable force on the electrode within a range of 5 g-50 g;

select a maximum allowable temperature, of tissue to be ablated, within a range of 55° C.-65° C.;

select an irrigation rate for providing irrigation fluid to the electrode within a range of 8-45 ml/min; and perform an ablation of tissue using the selected values by initially using the first power, switching to the second power after a predefined time between 3 s and 6 s, and terminating the ablation after a total time for the ablation between 10 s and 20 s.

There is further provided, according to an embodiment of the present invention, apparatus, including:

a power control module configured to perform an ablation procedure on biological tissue using radiofrequency (RF) power; and a processor configured to:

measure an impedance to the RF power during the procedure; and when a change in the impedance exceeds a preset value, halt supply of the RF power to the tissue.

There is further provided, according to an embodiment of the present invention, apparatus, including:

a power control module configured to perform an ablation procedure on biological tissue using radiofrequency (RF) power; and a processor configured to:

measure at respective times a temperature of the tissue; and when the temperature exceeds a preset maximum allowable temperature, reduce a level of the RF power supplied to the tissue.

The present disclosure will be more fully understood from the following detailed description of the embodiments thereof, taken together with the drawings, in which:

BRIEF DESCRIPTION OF THE DRAWINGS

FIGS. 2A, 2B, 2C, and 2D schematically illustrate a distal end of a probe used in the system, according to an embodiment of the present invention.

DETAILED DESCRIPTION OF EMBODIMENTS

Overview

Radiofrequency (RF) ablation in prior art systems is typically performed at continuous power levels of the order of 20-50 watts, with a contact force of approximately 10 g, and under irrigation. The time of ablation, depending on the size of the lesion to be achieved, is typically approximately 1 minute. In general, higher power levels reduce the time needed for forming a specific lesion. However, in prior art systems large values of continuous power, of approximately 100 watts, cannot be used because of the danger of steam pops being formed.

The inventors have found that there is a range of values of contact force and irrigation rate that allows continuous power of approximately 100 watts to be applied, and that within this range of values, a "sweet spot," no steam pops are formed. Application of this higher continuous power reduces the time required to form a given lesion.

For example, in a disclosed embodiment, a first RF power to be delivered to an electrode performing an ablation is selected to be in a range of 70 W-100 W, and a second RF power for the electrode is selected to be in a range of 20 W-60 W. An allowable contact force on the electrode is selected to be in a range of 5 g-50 g, a maximum allowable temperature of tissue to be ablated is selected to be in a range of 55° C.-65° C., and an irrigation rate for providing irrigation fluid to the electrode is selected within a range of 8-45 ml/min.

A lesion may be formed in the tissue using the selected values by initially using the first power, switching to the second power after a predefined time between 3 s and 6 s, and terminating the ablation after a total time for the ablation between 10 s and 20 s.

In embodiments of the present invention, during an ablation procedure the temperature of the tissue being ablated is carefully monitored and recorded at an extremely high rate. If the monitored temperature exceeds a preset maximum temperature limit, the RF power supplied to the tissue is reduced.

The impedance to the RF energy supplied to the tissue being ablated is also monitored. If the impedance increases by more than a preset value, the RF energy supply is halted.

The monitoring of the temperature and of the impedance allows embodiments of the present invention to perform tissue ablations at powers up to 100 W without adverse effects on the tissue during the ablation session. The high powers enable the ablation session to be shortened to times typically of no more than 10 s.

DETAILED DESCRIPTION

Figure 1:
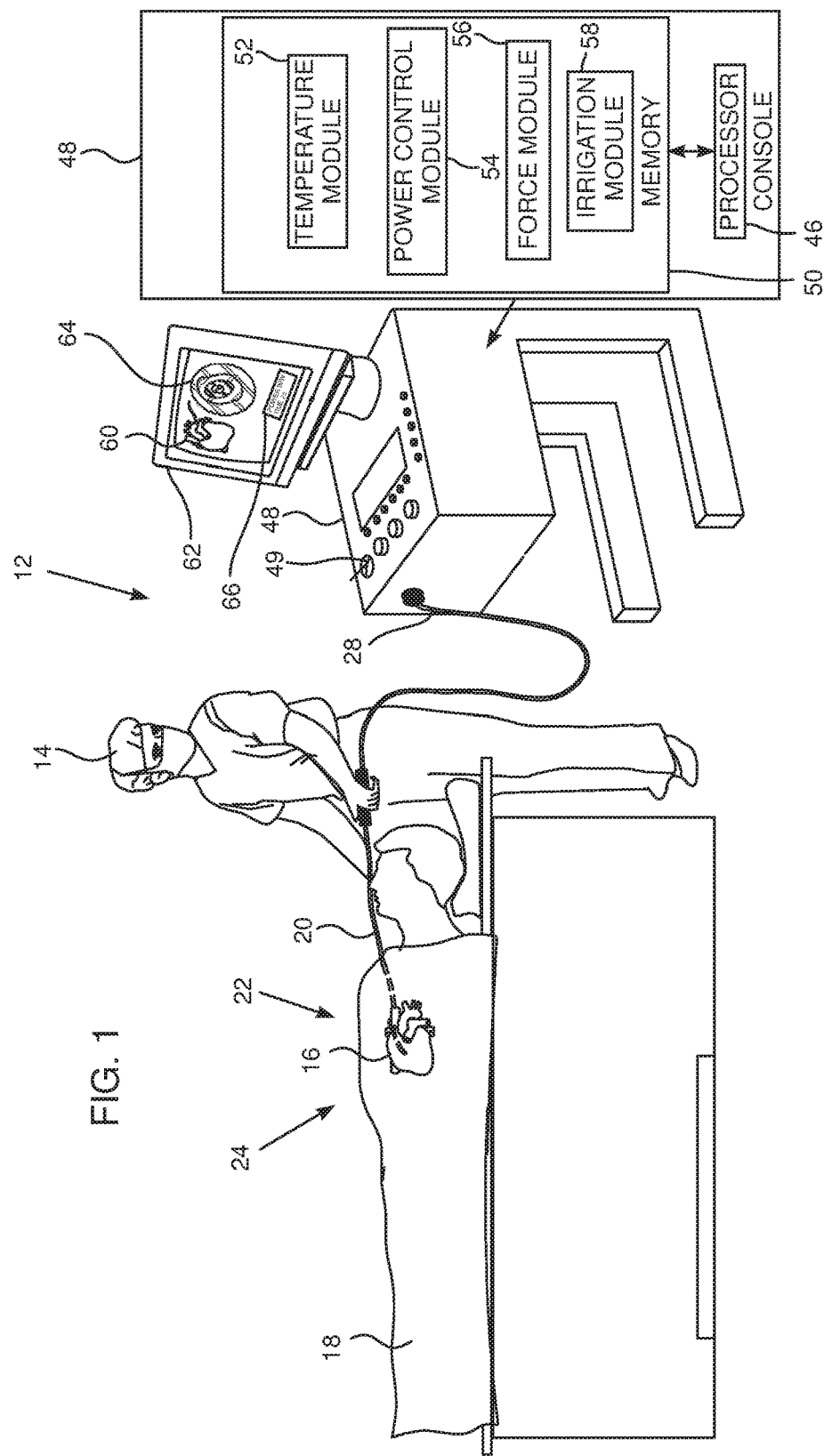
FIG. 1 is a schematic illustration of an ablation system, according to an embodiment of the present invention.

Reference is now made to FIG. 1, which is a schematic illustration of an invasive medical procedure using an ablation apparatus 12, according to an embodiment of the present invention. The procedure is performed by a physician 14, and, by way of example, the procedure in the description herein below is assumed to comprise ablation of a portion of a myocardium 16 of the heart of a human patient 18. However, it will be understood that embodiments of the present invention are not just applicable to this specific procedure, and may include substantially any ablation procedure on biological tissue.

In order to perform the ablation, physician 14 inserts a probe 20 into a lumen of the patient, so that a distal end 22 of the probe enters the heart of the patient. Distal end 22 comprises one or more electrodes 24 mounted on the outside of the distal end, the electrodes contacting respective locations of the myocardium. Probe 20 has a proximal end 28. Distal end 22 of the probe is described in more detail below with reference to FIGS. 2A, 2B, 2C and 2D.

Apparatus 12 is controlled by a system processor 46, which is located in an operating console 48 of the apparatus. Console 48 comprises controls 49 which are used by physician 14 to communicate with the processor. During the procedure, processor 46 typically tracks a location and an orientation of distal end 22 of the probe, using any method known in the art. For example, processor 46 may use a magnetic tracking method, wherein magnetic transmitters external to patient 18 generate signals in coils positioned in the distal end. The Carto® system produced by Biosense Webster, of Diamond Bar, Calif., uses such a tracking method.

The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 on a screen 62. The progress of the ablation performed with apparatus 12 is typically also displayed on screen 62, as a graphic 64 and/or alphanumeric data 66.

In order to operate apparatus 12, processor 46 communicates with a memory 50, which has a number of modules used by the processor to operate the apparatus. Thus, memory 50 comprises a temperature module 52, a power control module 54, a force module 56, and an irrigation module 58, the functions of which are described below. The modules may comprise hardware as well as software elements.

Figure 2D:
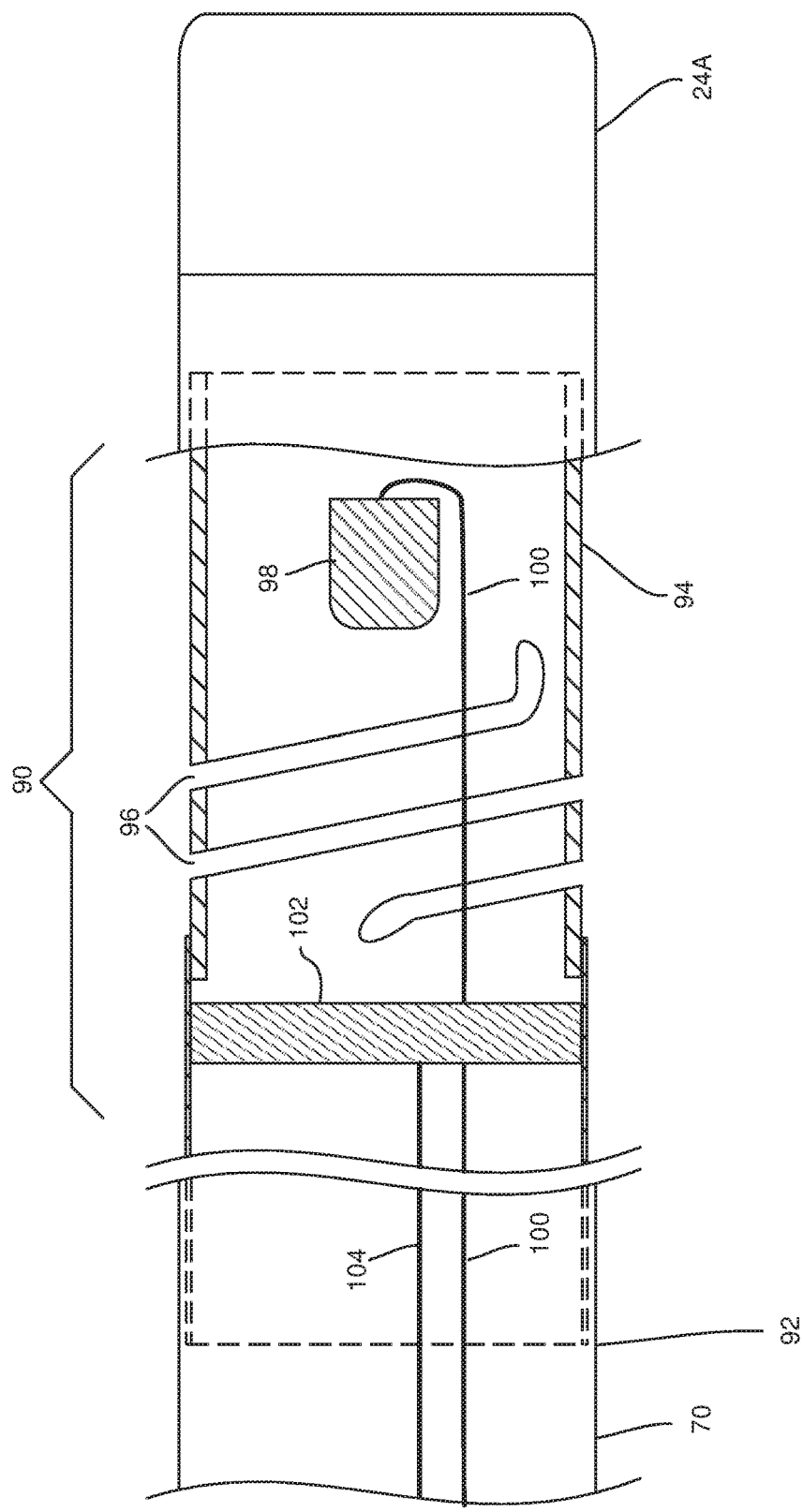

FIGS. 2A, 2B, 2C, and 2D schematically illustrate distal end 22 of probe 20, according to an embodiment of the present invention. FIG. 2A is a sectional view along the length of the probe, FIG. 2B is a cross-sectional view along a cut IIB-IIB that is marked in FIG. 2A, FIG. 2C is a perspective view of a section of the distal end and FIG. 2D is a schematic cross-sectional view of a force sensor 90 incorporated into a proximal portion 92 of the distal end. An insertion tube 70 extends along the length of the probe and is connected at the termination of its distal end to a conductive cap electrode 24A, which is used for ablation. Conductive cap electrode 24A is herein also termed the ablation electrode. Cap electrode 24A has an approximately plane conducting surface 84 at its distal end and a substantially circular edge 86 at its proximal end. Proximal to ablation electrode 24A there are typically other electrodes such as an electrode 24B. Typically, insertion tube 70 comprises a flexible, biocompatible polymer, while electrodes 24A, 24B comprise a biocompatible metal, such as gold or platinum, for example. Ablation electrode 24A is typically perforated by an array of irrigation apertures 72. In one embodiment there are 36 apertures 72, distributed evenly over electrode 24A.

An electrical conductor 74 conveys radio-frequency (RF) electrical energy from ablation module 54 (FIG. 1), through insertion tube 70, to electrode 24A, and thus energizes the electrode to ablate myocardial tissue with which the electrode is in contact. As described below, module 54 controls the level of RF power dissipated via electrode 24A. During the ablation procedure, irrigation fluid flowing out through apertures 72 irrigates the tissue under treatment, and the rate of flow of fluid is controlled by irrigation module 58. The irrigation fluid is delivered to electrode 24A by a tube (not shown in the diagram) within insertion tube 70.

Temperature sensors 78 are mounted within conductive cap electrode 24A at locations that are arrayed around the distal tip of the probe, both axially and circumferentially. In a disclosed embodiment considered herein, cap 24A contains six sensors, with one group of three sensors in a distal location, close to the tip, and another group of three sensors in a slightly more proximal location. This distribution is shown only by way of example, however, and greater or smaller numbers of sensors may be mounted in any suitable locations within the cap. Sensors 78 may comprise thermocouples, thermistors, or any other suitable type of miniature temperature sensor. Sensors 78 are connected by leads (not shown in the diagram) running through the length of insertion tube 70 to provide temperature signals to temperature module 52.

In a disclosed embodiment cap 24A comprises a side wall 73 that is relatively thick, on the order of 0.5 mm thick, in order to provide the desired thermal insulation between temperature sensors 78 and the irrigation fluid inside a central cavity 75 of the tip. The irrigation fluid exits cavity 75 through apertures 72. Sensors 78 are mounted on rods 77, which are fitted into longitudinal bores 79 in side wall 73. Rods 77 may comprise a suitable plastic material, such as polyimide, and may be held in place at their distal ends by a suitable glue 81, such as epoxy. U.S. Patent Application 2014/0171821, to Govari et al., whose disclosureh is incorporated herein by reference, describes a catheter having temperature sensors mounted in a similar configuration to that described above. The arrangement described above provides an array of six sensors 78, but other arrangements, and other numbers of sensors, will be apparent to those having ordinary skill in the art, and all such arrangements and numbers are included within the scope of the present invention.

In the description herein, distal end 22 is assumed to define a set of xyz orthogonal axes, where an axis 94 of the distal end corresponds to the z axis of the set. For simplicity and by way of example, the y axis is assumed to be in the plane of the paper, the xy plane is herein assumed to correspond to the plane defined by circle 86, and the origin of the xyz axes is assumed to be the center of the circle.

FIG. 2D is a schematic, sectional view of force sensor 90, according to an embodiment of the present invention. Sensor 90 comprises a spring 94, herein assumed to comprise a plurality of helices 96, connecting cap 24A to proximal end 92. A position sensor 98 is fixed to the distal side of spring 94, and is herein assumed to comprise one or more coils coupled by conductors 100 to force module 56.

An RF transmitter 102, typically a coil, is fixed to the proximal side of spring 94, and the RF energy for the transmitter is provided from force module 56 via conductors 104. The RF energy from the transmitter traverses sensor 98, generating a corresponding signal in conductors 100 of the sensor.

In operation, as force is exerted on cap 24A sensor 98 moves relative to transmitter 102, and the movement causes a change in the signals of the sensor. Force module 56 uses the change in signal of the sensor to provide a metric of the force on cap 24A. The metric typically provides the force in magnitude and direction.

A more detailed description of a sensor similar to sensor 90 is provided in US Patent Application 2011/0130648, which is incorporated herein by reference.

Returning to FIG. 1, temperature module 52 receives signals from the six sensors 78 within cap 24A, and uses the signals to determine a maximum value of the six measured temperatures. The temperature module is configured to calculate the maximum temperature at a fixed rate, herein assumed to be every 33 ms, but other embodiments may calculate the maximum temperature at higher or lower rates. In some embodiments the maximum temperature is determined at a frequency of at least 30 Hz. The calculated maximum temperature is herein also termed the measured temperature, and the measured temperature is registers the temperature of the tissue being ablated. The temperature module passes the measured temperature value to power control module 54.

Power control module 54 provides RF power to cap 24A in a range of 1 W to 100 W. In embodiments of the present invention the module can be configured to provide a maximum RF power to cap 24A that can be set within a range of 70 W-100 W. In some embodiments, the module can be configured to provide a further RF power to cap 24A in a different range from the maximum. In one embodiment the further power range is 20 W-60 W, and the further power is typically provided after the maximum power. The maximum RF power and the further RF power are also termed herein the first power and the second power.

The power control module also measures an impedance of cap 24A. The impedance is measured at a predefined rate, herein assumed to be every 500 ms, but other embodiments may measure the impedance at a lower or higher rate.

The maximum power, and the time period for which the power is delivered, is selected by physician 14. The physician may also select values of the power less than 70 W, and corresponding time periods for delivery of this reduced power. The actual power delivered is determined by the measured temperature received from temperature module 52, as described below.

Typically, during an ablation session, the impedance of cap 24A decreases. Embodiments of the present invention also check if the impedance increases from a previous impedance measurement by more than a pre-set value, herein assumed to be 7Ω, although other embodiments may use larger or smaller values of impedance increase for the pre-set value. An increase of impedance typically occurs if there is an unwanted change in the tissue being ablated, such as charring or steam popping. If the impedance increases by more than the pre-set value, the power control module is configured to stop the RF delivery to cap 24A.

Notwithstanding the powers selected by the physician, the power control module is configured to reduce the power delivered, typically by between approximately 5% and approximately 95%, if the measured temperature received from the temperature module reaches or exceeds a maximum allowable temperature that is set by physician 14.

In one embodiment, power that has been originally set to 90 W is reduced to 50 W after 4 s, regardless of the readings from sensors 78. In an embodiment of the present invention, the maximum allowable temperature may be set within a range 60° C.-65° C. Typically, exceeding the maximum allowable temperature causes undesirable effects such as charring, coagulation on cap 24A, and/or steam pops in the tissue being ablated.

As explained above, force module 56 is able to measure the force on cap 24A. In an embodiment, the allowable force for an ablation is in the range of 5 g-35 g.

Irrigation module 58 governs the rate at which irrigation fluid is delivered to the catheter tip. In some embodiments of the present invention it may be set within the range of 8-45 ml/min.

Figure 3:
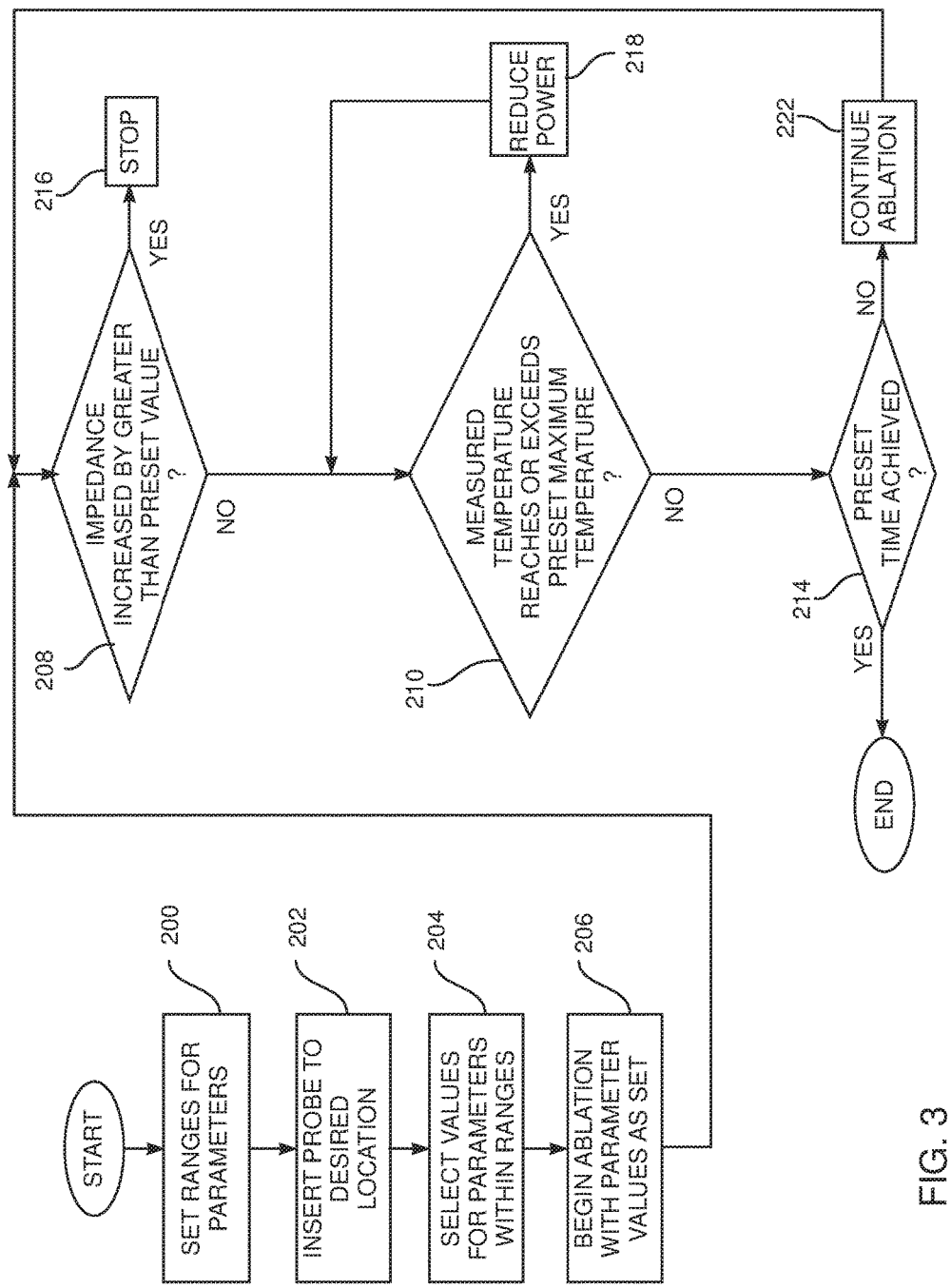
FIG. 3 is a flowchart of steps performed during an ablation session using the system.

FIG. 3 is a flowchart of steps performed in operation of apparatus 12 during an ablation session, according to an embodiment of the present invention. In an embodiment of the present invention, an ablation session comprises two time periods: a first time period during which a first target power applies, followed by a second time period during which a second target power applies. In some ablation sessions only the first time period is used, and in this case there is only one target power set. The target powers within each time period are maximum RF powers which may be delivered by power control module 54.

In a range setting step 200, ranges for each of the variable parameters referred to above are set. In one embodiment the ranges are set as shown in Table I. Typically, for the target powers, an operator of the system only sets the first target power, while the second power is automatically set by the system.

TABLE I

| Parameter | Range |
| --- | --- |
| First Target Power | 70 W-100 W |
| Second Target Power | 20 W-60 W |
| Allowable Force | 5 g-50 g |
| Maximum allowable temperature | 55° C.-65° C. |
| Irrigation rate | 8-45 ml/min |
| First Time Period (during which First Target Power is operative) | 1 s to 6 s |
| Second Time Period (during which Second Target Power is operative) | Up to 14 s |
| Overall Time Period for Power Delivery (Sum of First and Second Time Periods) | 1 s-20 s |

Range setting step 200 is implemented before physician 14 performs an ablation.

At the beginning of an ablation session, in a probe introduction step 202, physician 14 inserts probe 20 into a desired location in myocardium 16, using the tracking system incorporated into apparatus 12.

In a select value step 204, prior to performing the ablation procedure, physician 14 selects values of the parameters listed in Table I that are to be used in the procedure, and uses controls 49 to provide the values to the system. Alternatively, the physician selects a predetermined set of the values of the parameters listed in Table I, typically by choosing a "recipe," comprising the values, from a group of such recipes. The selected values typically depend on the depth of lesion it is desired to form by the procedure. For lesions of 1-3 mm depth the inventors have found that the values of the parameters given by Table II give good results. For lesions of 4-5 mm depth the inventors have found that the values of the parameters given by Table III give good results.

TABLE II

Lesions of 1-3 mm Depth

| Parameter | Value |
| --- | --- |
| First Target Power | 90 W |
| Second Target Power | Not set |
| Allowable Force | 10 g-20 g |
| Maximum allowable temperature | 60° C. |
| Irrigation rate | 15 ml/min |
| First Time Period | 3 s |
| Second Time Period | Not set |

TABLE III

Lesions of 4-5 mm Depth

| Parameter | Value |
| --- | --- |
| First Target Power | 90 W |
| Second Target Power | 50 W |
| Allowable Force | 10 g-20 g |
| Maximum allowable temperature | 60° C. |
| Irrigation rate | 15 ml/min |
| First Time Period | 3 s |
| Second Time Period | 7 s |

Those having ordinary skill in the art will be able to determine, for other lesion depths, required values of the parameters within the ranges given by Table I, without undue experimentation.

In a begin RF delivery step 206, the first time period of the ablation session begins, by physician 14 initiating operation of apparatus 12. The ablation session uses the parameter values selected in step 204, in order to perform the ablation. Typically, during the ablation session, screen 62 displays values of the parameters listed in Table I to the physician. Screen 62 may also be configured to display to the physician, by methods which are known in the art, the progress of the RF delivery. The display of the progress may be graphical, such as a simulation of the dimensions of the lesion as it is produced by the ablation, and/or alphanumeric.

The remaining steps of the flowchart apply for both the first time period, and, if operative, for the second time period.

During the RF delivery procedure the system uses the power control module to perform a number of checks on the progress of the procedure, as shown in the flowchart by decision steps 208, 210, and 214.

In step 208, the power control module checks if the impedance to the delivered RF power of cap 24A has increased by more than the pre-set impedance value. If it has, the system halts the procedure in a termination step 216. If step 208 returns a negative value, control of the flowchart continues to decision step 210.

In step 210, the power control module checks if the measured temperature exceeds or reaches the pre-set maximum allowable temperature selected in step 204. If decision step 210 returns a positive value, the power control module, in a power reduction step 218, reduces the power to cap 24A.

The power reduction in step 218 is a function of a number of parameters:

A difference in temperature between the maximum allowable temperature T (set in step 204) and the measured temperature $T_t$ at a time t, A change of measured temperatures between sequential temperature measurements, i.e., $T_{t-1}-T_t$, A target power P, where if the flowchart is functioning in the first time period, P is the first target power, and if the flowchart is functioning in the second time period, P is the second target power, and A power $P_t$ measured at time t.

In one embodiment the following equations applies for the power reduction:

$$\Delta P(T) = \frac{a(T_{t-1} - T_t)}{T} + \frac{b(T - T_t)}{T} \quad (1)$$

where $\Delta P(T)$ is a fractional change in power as a function of temperature, and a and b are numerical constants. In a disclosed embodiment a=10 and b=1.

$$\Delta P(p) = \frac{(P - P_t)}{P} \quad (2)$$

where $\Delta P(p)$ is a fractional change in power as a function of power.

$$\Delta P = \min(\Delta P(T), \Delta P(p)) \quad (3)$$

where min($\Delta P(T)$, $\Delta P(p)$) is the minimum of $\Delta P(T)$ and $\Delta P(p)$, and $\Delta P$ is the fractional change in power applied in step 218.

Typically, power reduction step 218 is performed reiteratively with decision step 210, until the measured temperature is below the preset maximum temperature.

If step 210 returns a negative value, control continues to decision step 214.

In decision step 214, the system checks if the overall time period for the ablation session, set in step 204, has been reached. If it has, then the flowchart ends. In decision step 214, the system also checks if the end of the first time period has been reached, and if it has, the system enters the second time period.

If the overall time period has not been reached, control passes to a continuing ablation step 222, where the system continues the ablation, and returns to decision steps 208, 210, and 214. Decision steps 208, 210, and 214 have been presented sequentially in the flowchart for simplicity and clarity. Typically, however, the system uses the power control module to perform the steps in parallel.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising: defining a preset impedance value I; performing an ablation procedure on biological tissue using radiofrequency (RF) power; measuring an impedance $I_{T-1}$ to the RF power during the ablation procedure at time (T−1); measuring an impedance $I_T$ to the RF power during the ablation procedure at time (T); and when a difference between impedance $I_T$ and $I_{T-1}$ exceeds the preset impedance value I, halting supply of the RF power to the tissue.

2. The method of claim 1, wherein the preset impedance value I is 7 ohms.

3. The method of claim 1, further comprising measuring temperature of the tissue when the difference between impedance $I_{T-1}$ and $I_T$ is not greater than the preset impedance value I.

4. The method of claim 3, wherein the measuring temperature of the tissue occurs at a frequency of at least 30 Hz.

5. The method of claim 4, wherein the reducing supply of the RF power includes reducing supply of the RF power by a range between about 5% 95%.

6. The method of claim 1, further comprising reducing supply of the RF power to the tissue when a measured temperature of the tissue reaches or exceeds a preset maximum temperature value.

7. Apparatus, comprising: a power control module configured to perform an ablation procedure on biological tissue using radiofrequency (RF) power; and a processor configured to: measure an impedance $I_{T-1}$ to the RF power during the procedure at time (T−1); measure an impedance $I_T$ to the RF power during the procedure at time (T); and when difference between impedance $I_{T-1}$ and $I_T$ exceeds a preset impedance value, halt supply of the RF power to the tissue.

8. The apparatus of claim 7, wherein the preset impedance value is 7 ohms.

9. The apparatus of claim 7, wherein the processor is configured to measure temperature of the tissue when the difference between impedance $I_{T-1}$ and $I_T$ is not greater than the preset impedance value.

10. The method of claim 9, wherein the processor is configured to measure temperature of the tissue at a frequency of at least 30 Hz.

11. The apparatus of claim 7, wherein the processor is configured to reduce supply of the RF power to the tissue when a measured temperature of the tissue reaches or exceeds a preset maximum temperature value.

12. The apparatus of claim 11, wherein the processor is configured to reduce supply of the RF by a range between about 5% 95%.

13. A method, comprising: defining a preset impedance value I; performing an ablation procedure on biological tissue using radiofrequency (RF) power at a power up to about 100 W with a duration of no greater than 10 seconds; measuring an impedance $I_{T-1}$ to the RF power during the ablation procedure at time (T−1); measuring an impedance $I_T$ to the RF power during the ablation procedure at time (T); and when a difference between impedance $I_T$ and $I_{T-1}$ exceeds the preset impedance value I, halting supply of the RF power to the tissue.

14. The method of claim 13, wherein the impedances $I_{T-1}$ and $I_T$ are measured at a rate of about every 500 ms.

15. Apparatus, comprising: a power control module configured to perform an ablation procedure on biological tissue using radiofrequency (RF) power; and a processor configured to: perform the ablation procedure on the biological tissue using the radiofrequency (RF) power at a power up to about 100 W with a duration of no greater than 10 seconds; measure an impedance $I_{T-1}$ to the RF power during the procedure at time (T−1); measure an impedance $I_T$ to the RF power during the procedure at time (T); and when difference between impedance $I_{T-1}$ and $I_T$ exceeds a preset impedance value, halt supply of the RF power to the tissue.

16. The apparatus of claim 15, wherein the processor is configured to measure the impedances $I_{T-1}$ and $I_T$ at a rate of about every 500 ms.

* * * * *